(12) United States Patent
Kim et al.

(10) Patent No.: US 9,644,177 B2
(45) Date of Patent: May 9, 2017

(54) EXTRACELLULAR MATRIX FILMS AND METHODS OF MAKING AND USING SAME

(71) Applicant: Board of Regents, The University of Texas System, Austin, TX (US)

(72) Inventors: Young-Tae Kim, Arlington, TX (US); Sreevidhya Banda, Arlington, TX (US); Deepika Tamuly, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 49 days.

(21) Appl. No.: 13/940,739

(22) Filed: Jul. 12, 2013

(65) Prior Publication Data

US 2014/0024117 A1  Jan. 23, 2014

Related U.S. Application Data

(60) Provisional application No. 61/670,685, filed on Jul. 12, 2012.

(51) Int. Cl.
*C12N 5/00* (2006.01)
*C12N 5/02* (2006.01)
*C12M 1/12* (2006.01)

(52) U.S. Cl.
CPC ........... *C12N 5/0068* (2013.01); *C12M 25/14* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 4,215,693 A * | 8/1980 | Rothman et al. | ............ | 604/368 |
| 4,505,855 A * | 3/1985 | Bruns | ............ | A61F 2/14 128/DIG. 8 |
| 4,581,030 A * | 4/1986 | Bruns | ............ | A61F 2/14 128/DIG. 8 |
| 4,983,181 A * | 1/1991 | Civerchia | ............ | A61F 2/14 128/DIG. 8 |
| 4,994,081 A * | 2/1991 | Civerchia | ............ | A61F 2/14 606/107 |
| 5,112,350 A * | 5/1992 | Civerchia | ............ | A61F 2/14 606/107 |
| 5,114,627 A * | 5/1992 | Civerchia | ............ | A61F 2/14 264/1.1 |
| 5,667,961 A * | 9/1997 | Bernard et al. | ............ | 435/1.1 |
| 5,837,278 A * | 11/1998 | Geistlich | ............ | A61L 15/325 424/402 |
| 7,195,912 B2 * | 3/2007 | Takezawa | ............ | A61L 31/005 435/395 |
| 2001/0008930 A1 * | 7/2001 | Tayot | ............ | A61L 31/041 527/200 |
| 2002/0009796 A1 * | 1/2002 | Goodwin, Jr. | ............ | 435/288.7 |
| 2002/0086423 A1 * | 7/2002 | Takezawa et al. | ............ | 435/397 |
| 2002/0160036 A1 * | 10/2002 | Geistlich | ............ | A61L 31/044 424/443 |
| 2003/0133967 A1 * | 7/2003 | Ruszczak | ............ | A61L 15/325 424/443 |
| 2003/0203485 A1 * | 10/2003 | Takezawa et al. | ............ | 435/395 |
| 2004/0219184 A1 * | 11/2004 | Brown et al. | ............ | 424/423 |
| 2004/0235151 A1 * | 11/2004 | Doge | ............ | C12M 35/02 435/289.1 |
| 2005/0129720 A1 * | 6/2005 | Takezawa et al. | ............ | 424/400 |
| 2006/0177492 A1 * | 8/2006 | Yunoki | ............ | A61K 9/06 424/445 |
| 2008/0181935 A1 * | 7/2008 | Bhatia et al. | ............ | 424/443 |
| 2008/0287342 A1 * | 11/2008 | Yu | ............ | A61K 38/10 514/1.1 |
| 2009/0035855 A1 * | 2/2009 | Ying et al. | ............ | 435/377 |
| 2009/0069893 A1 * | 3/2009 | Paukshto et al. | ............ | 623/13.11 |
| 2009/0312524 A1 * | 12/2009 | Lauritzen | ............ | A61K 38/17 530/356 |
| 2010/0168808 A1 * | 7/2010 | Citron | ............ | 607/5 |
| 2011/0282448 A1 * | 11/2011 | Paulos et al. | ............ | 623/13.11 |
| 2014/0081070 A1 * | 3/2014 | Paukshto | ............ | A61L 27/04 600/13 |

OTHER PUBLICATIONS

Barnes et al., Biomater., 32(1):137-143 (2011).*
Brown et al., Biomater., 31(3):428-437 (2010).*
Langenbach et al., BMC Biotechnol., 6(14):1-14 (2006).*
Lu et al., Biomater., 28:1486-1494 (2007).*
Nowatzki et al., Biomater., 25:1261-1267 (2004).*
Zhang et al., Biomater., 26:3353-3361 (2005).*
Ambrose et al., J. Biomed. Mater. Res. B, 90B:818-831 (2009).*
Wang et al., J. Biosci. Bioeng., 99(6):529-540 (2005).*
Yoshizato et al., J. Cell Sci., 91:491-499 (1988).*
Lawrence et al., J. Vis. Exp. 62(e3646):1-6 (2012).*
Gunja et al., J. Tiss. Eng. Ren. Med., 3:521-530 (2009).*
Crabb, Rachael Anne Bergstrom, "Collagen Processing for Tissue-Engineered Corneas: Influence on Optical and Biomechanical Properties", Thesis submitted to the University of Minnesota, Jan. 2007, 121 pages.
Bhatia et al., Partial USPTO Prosecution History for U.S. Appl. No. 13/212,661, filed Aug. 18, 2011, 112 pages.
Takezawa et al., Partial USPTO Prosecution History for U.S. Appl. No. 11/035,954, filed Jan. 18, 2005, 35 pages.

* cited by examiner

*Primary Examiner* — Thomas J Visone
(74) *Attorney, Agent, or Firm* — John P. Zimmer; Smith Moore Leatherwood LLP

(57) ABSTRACT

In one aspect, films that can serve as a model or mimic for the basal lamina are described herein. In some embodiments, a film described herein comprises a top surface and a bottom surface in facing opposition to the top surface, wherein the film is formed from Type I collagen and one or more additional extracellular matrix proteins. The additional extracellular matrix proteins, in some cases, comprise one or more of Type IV collagen, laminin, and fibronectin. Moreover, in some instances, the weight ratio of Type I collagen to the additional extracellular matrix proteins in the film is at least about 40:1.

21 Claims, 6 Drawing Sheets

EXTRACELLULAR MATRIX FILMS AND METHODS OF MAKING AND USING SAME

CROSS REFERENCE TO RELATED APPLICATION

This application claims priority pursuant to 35 U.S.C. §119(e) to U.S. Provisional Patent Application Ser. No. 61/670,685, filed on Jul. 12, 2012, which is hereby incorporated by reference in its entirety.

FIELD

This invention relates to films and, in particular, to films formed from Type I collagen and one or more additional extracellular matrix proteins.

BACKGROUND

The basal lamina is an integral component of the human body. It is composed of nearly 50 different proteins, including collagens and laminin. The basal lamina provides structural support to tissue, facilitates cell differentiation and migration, and mediates various intercellular interactions. Recently, the importance of the basal lamina has encouraged the development of artificial models or mimics for one or more components of the basal lamina. However, some existing models or mimics include only a limited number of proteins and/or cannot be provided as self-supporting or free-standing films. In addition, some existing models or mimics cannot be easily combined to form more complex structures such as three-dimensional articles having a complex compositional gradient.

Therefore, there exists a need for engineered films that can more closely approximate the basal lamina and/or provide one or more additional features desirable for use with cells in vitro and/or in vivo.

SUMMARY

In one aspect, films that can serve as a model or mimic for the basal lamina and/or be used to form complex three-dimensional structures are described herein. Films described herein, in some cases, can also provide one or more advantages not provided by other films. In some embodiments, a film described herein comprises a top surface and a bottom surface in facing opposition to the top surface, wherein the film is formed from Type I collagen and one or more additional extracellular matrix (ECM) proteins. The additional ECM proteins, in some embodiments, comprise one or more of Type IV collagen, laminin, vitronectin, and fibronectin. In some embodiments, the additional ECM proteins comprise chondroitin sulfate proteoglycans (CSPGs). Moreover, in some cases, the weight ratio of Type I collagen to the additional extracellular matrix proteins in the film is at least about 40:1. Additionally, in some instances, a film described herein further comprises a drug or antibody. In some cases, a film described herein further comprises a plurality of cells disposed on a surface of the film, such as the top surface of the film.

A film described herein, in some cases, can exhibit one or more desirable properties. In some embodiments, for instance, a film described herein can be a free-standing or self-supporting film, including a solid free-standing or self-supporting film. Moreover, such a film, in some cases, can be peelable. In some embodiments, a film described herein can also be semi-permeable, smooth, and/or optically transparent. In some cases, a film described herein can have an average thickness of about 100 nm to about 20 μm. Further, in some instances, one or more films described herein can be used to construct a three-dimensional tissue scaffold or tissue model or a stack of films having a gradient of properties, as described further hereinbelow. Moreover, in some cases, films described herein can be stacked with one another to provide a three-dimensional article or stack of films without the use of a glue or adhesive.

In another aspect, methods of making a film are described herein. In some embodiments, a method of making a film comprises combining a first solution comprising Type I collagen with a second solution comprising one or more ECM proteins to provide a gel solution. The method further comprises disposing the gel solution in a mold and drying the gel solution in the mold to provide the film. In some embodiments, a method of making a film described herein further comprises crosslinking the one or more ECM proteins. A method described herein can also comprise removing the film from the mold, such as by peeling the film out of the mold. Moreover, in some cases, a method described herein further comprises washing and/or sterilizing the film.

In yet another aspect, articles comprising a film or a stack of films are described herein. In some embodiments, an article comprises a stack of films, wherein at least one film of the stack is a film described herein. For example, in some cases, at least one film of the stack is formed from Type I collagen and one or more additional ECM proteins. In some cases, a plurality of films of the stack are films described herein. For example, in some cases, a stack of films comprises (1) a first film comprising a first top surface, a first bottom surface in facing opposition to the first top surface, and a first plurality of cells disposed on the first top surface of the first film and (2) a second film comprising a second top surface, a second bottom surface in facing opposition to the second top surface, and a second plurality of cells disposed on the second top surface of the second film, wherein the first and second films are arranged in a stacked configuration and are each formed from Type I collagen and one or more additional ECM proteins.

However, stacks of films described herein are not limited to stacks comprising two films described herein. Instead, if desired, stacks of films described herein can further comprise any desired number of additional films described herein. Thus, articles described herein, in some embodiments, can comprise a stack of three films, four films, five films, or more than five films described herein. Moreover, in some cases, a stack of films described herein is free or substantially free of a glue or adhesive material disposed between the films. Further, in some cases, a stack of films described herein can be rolled into a tubular shape. Thus, in some cases, an article described herein can be a vascular graft or model for a biological organ or compartment such as a blood vessel. In other cases, an article can be an air-blood barrier model in lung tissue or a blood-brain barrier model in brain and spinal cord tissue.

Additionally, in some embodiments, an article described herein comprises a film described herein in combination with another film or material. For example, in some cases, an article described herein comprises a first film formed from Type I collagen and one or more additional ECM proteins and a second film formed from a hydrogel, wherein the first film and the second film have differing mechanical stiffness and are immediately adjacent to one another in a stacked configuration. In other embodiments, an article described herein comprises a film described herein, a first block comprising a first microchannel, and a second block comprising a second microchannel, wherein the film is disposed between and immediately adjacent to the first block and the second block and the first microchannel and the second microchannel are in fluid communication with the film. Further, in some cases, the film of such an article comprises a semi-permeable film described herein, such as a film that is permeable to air but is not permeable to liquids such as blood. Thus, in some embodiments, an article described herein can be a microfluidic device wherein a film described herein acts as a semi-permeable membrane between microchannels or micro-patterned blocks disposed on opposite sides of the membrane film.

In another aspect, methods of making a stack of films are described herein. In some embodiments, a method of making a stack of films comprises providing a first film described herein; providing a second film described herein; wetting the top surface of the first film with water; and stacking the second film on top of the first film, wherein the bottom surface of the second film contacts the water disposed on the top surface of the first film to provide a wet interface between the stacked first and second films. In some embodiments, a method of making a stack of films further comprises drying the interface between the stacked first and second films. Further, in some cases, a method described herein can also comprise providing one or more additional films described herein and repeating the wetting, stacking, and drying steps to provide a stack of films comprising any desired number of films. Therefore, a method of making a stack of films described herein, in some embodiments, can provide a stack of films suitable for use as a tissue scaffold, cell culture substrate, and/or tissue model, including a scaffold, cell culture substrate, and/or tissue model having a complex or layered configuration of cell types. Moreover, methods of making a stack of films described herein, in some embodiments, do not comprise disposing a glue or adhesive material between films of the stack.

DETAILED DESCRIPTION

Figure 1:
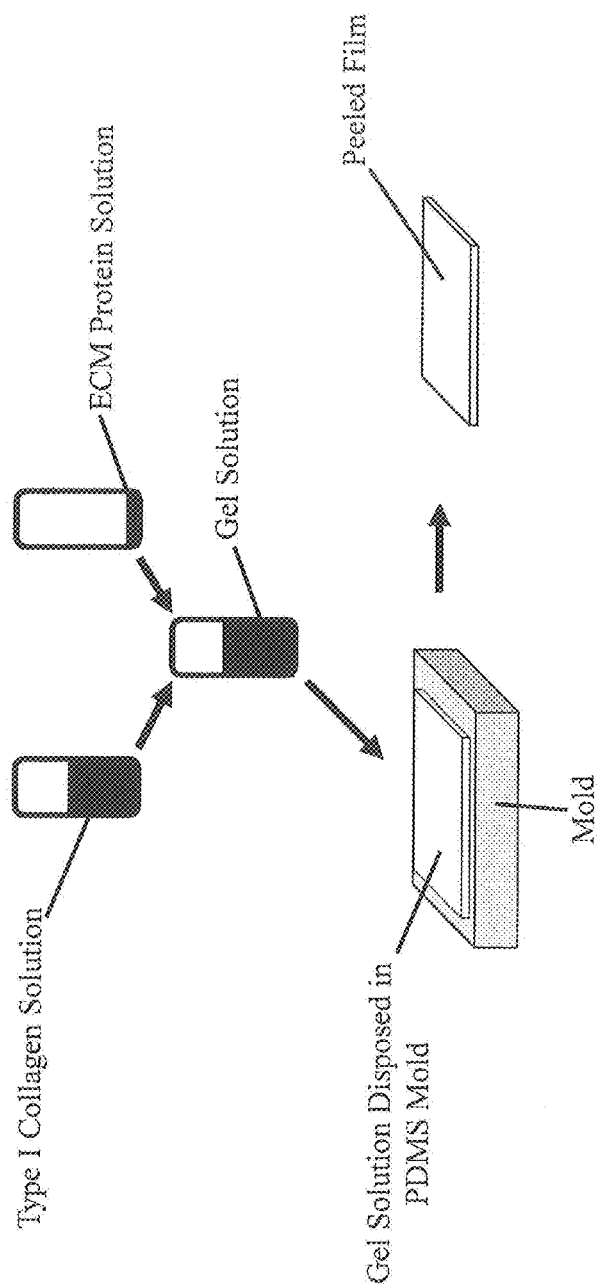
FIG. 1 illustrates a perspective view of some steps of a method of making a film according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Films

In one aspect, films are described herein. In some embodiments, a film comprises a top surface and a bottom surface in facing opposition to the top surface, wherein the film is formed from Type I collagen and one or more additional ECM proteins. A film formed from Type I collagen and one or more additional ECM proteins described herein, in some cases, is formed from a composite material comprising, consisting of, or consisting essentially of Type I collagen, one or more additional ECM proteins, and water. Further, in some instances, the composite material used to form a film described herein does not comprise a Type I collagen crosslinker. A "Type I collagen crosslinker," for reference purposes herein, comprises a chemical species (such as glutaraldehyde) operable to crosslink Type I collagen.

Additionally, in some instances, a film described herein further comprises a drug and/or antibody. The drug and/or antibody can be dispersed throughout the film or disposed on a surface of the film. Moreover, in some cases, a film described herein further comprises a plurality of cells disposed on a surface of the film, such as the top surface of the film.

Turning now to components of films, films described herein are formed from Type I collagen. Any Type I collagen not inconsistent with the objectives of the present invention may be used. In some embodiments, for example, Type I collagen comprises rat tail collagen. However, Type I collagen derived from other sources (such as bovine skin) may also be used. Moreover, in some cases, the Type I collagen of a film described herein is not crosslinked. In addition, in some embodiments, the Type I collagen of a film described herein comprises collagen fibrils. The collagen fibrils of the film, in some instances, are aligned or substantially aligned with one another. A film comprising "substantially aligned" Type I collagen fibrils, for reference purposes herein, exhibits an alignment of the long axes of at least about 60 percent, at least about 70 percent, at least about 80 percent, at least about 90 percent, or at least about 95 percent of the collagen fibrils of the film within about 10 degrees or within about 5 degrees of the average long axis direction of the aligned fibrils.

Type I collagen can be present in a film described herein in any amount not inconsistent with the objectives of the present invention. In some cases, Type I collagen comprises up to about 60 weight percent, up to about 70 weight percent, up to about 80 weight percent, up to about 90 weight percent, up to about 95 weight percent, or up to about 99 weight percent of the film, based on the total weight of the film. In some embodiments, Type I collagen comprises from about 30 weight percent to about 99 weight percent, from about 50 weight percent to about 99 weight percent, from about 60 weight percent to about 99 weight percent, from about 70 weight percent to about 99 weight percent, from about 80 weight percent to about 99 weight percent, or from about 90 weight percent to about 99 weight percent of the film, based on the total weight of the film.

Films described herein are also formed from one or more additional ECM proteins. "Additional" ECM proteins, for reference purposes herein, comprise ECM proteins in addition to the Type I collagen of the film. Any ECM proteins not inconsistent with the objectives of the present invention may be used. In some cases, the additional ECM proteins comprise one or more of Type IV collagen, laminin, vitronectin, and fibronectin. In some embodiments, the additional ECM proteins comprise chondroitin sulfate proteoglycans (CSPGs). Moreover, in some cases, the additional ECM proteins comprise a mixture of proteins such as Matrigel™.

The additional ECM proteins can be present in a film described herein in any amount not inconsistent with the objectives of the present invention. In some cases, the additional ECM proteins comprise up to about 20 weight percent, up to about 10 weight percent, up to about 5 weight percent, up to about 1 weight percent, or up to about 0.5 weight percent of the film, based on the total weight of the film. In some embodiments, the additional ECM proteins comprise from about 1 weight percent to about 20 weight percent, from about 1 weight percent to about 10 weight percent, from about 1 weight percent to about 5 weight percent, or from about 2 weight percent to about 5 weight percent of the film, based on the total weight of the film.

Further, the Type I collagen and additional ECM proteins of a film described herein can be present in the film in any amount relative to one another not inconsistent with the objectives of the present invention. For example, in some instances, the weight ratio of Type I collagen to the additional ECM proteins is at least about 40:1 or at least about 50:1. In some embodiments, the weight ratio of Type I collagen to the additional ECM proteins is between about 40:1 and about 80:1, between about 40:1 and about 70:1, between about 40:1 and about 60:1, or between about 45:1 and about 55:1.

Films described herein, in some cases, also comprise a drug and/or antibody dispersed throughout the film or disposed on a surface of the film. Any drug and/or antibody not inconsistent with the objectives of the present invention may be used. For example, in some embodiments, a drug comprises an anti-cancer drug such as Taxol. In some cases, a drug described herein is water-soluble and/or soluble in dimethyl sulfoxide (DMSO).

A film described herein, in some embodiments, can also comprise a plurality of cells disposed on the top surface of the film. Any cells not inconsistent with the objectives of the present invention may be used. In some embodiments, the cells comprise cultured cells such as cultured animal cells or cultured bacteria cells. In some cases, the cells comprise epithelial cells, lung cells, brain cells, or blood cells of an animal such as a human. In some embodiments, the cells comprise cancer cells such as breast cancer cells or human glioblastoma (GBM) brain cancer cells. Moreover, the cells of a film described herein can be living or non-fixed cells.

Films described herein, in some embodiments, can exhibit one or more desirable properties. In some embodiments, for instance, a film described herein can be a free-standing or self-supporting film, including a solid free-standing or self-supporting film. A "free-standing" or "self-supporting" film, for reference purposes herein, comprises a film that has sufficient mechanical strength and/or integrity to maintain or substantially maintain its size and shape when removed from a substrate on which the film was formed. Moreover, such a film, in some cases, can be peelable. A "peelable" film, for reference purposes herein, refers to a film that has sufficient mechanical strength and/or integrity to be removed or peeled from a substrate on which the film was formed without breaking the film.

In some embodiments, a film described herein can also be semi-permeable. A "semi-permeable" film, as understood by one of ordinary skill in the art, comprises a film that allows some chemical species (such as specific molecules or ions) to pass through the film by diffusion but does not allow other chemical species to diffuse through the film. In some embodiments, for example, a film described herein is permeable to oxygen but not water. In other cases, a film described herein is permeable to both oxygen and water. The permeability or semi-permeability of a film described herein, in some cases, can be selected based on the amount of Type I collagen used to form the film. For example, in some embodiments, a film comprising a relatively high amount of Type I collagen can be permeable to air but not to water, and a film comprising a relatively low amount of Type I collagen can be permeable to both air and water, as described further hereinbelow. A semi-permeable film described herein, in some embodiments, can therefore be used as a selectively permeable membrane.

In addition, a film described herein, in some embodiments, can also be smooth or have a smooth surface. For instance, in some cases, a film described herein has a surface roughness $R_a$ of about 50 nm to about 250 nm when measured as described herein. In some embodiments, a film described herein has a surface roughness $R_a$ of about 70 nm to about 230 nm, about 90 nm to about 210 nm, about 100 nm to about 200 nm, or about 125 nm to about 175 nm when measured as described herein.

A film described herein can also have any thickness not inconsistent with the objectives of the present invention. In some embodiments, a film described herein is a thin film. In some cases, a film has an average thickness of about 100 nm to about 20 µm or about 100 nm to about 10 µm. In some embodiments, a film described herein has an average thickness of about 200 nm to about 5 µm, about 250 nm to about 3 µm, about 250 nm to about 1.5 µm, or about 300 nm to about 1 µm. The average "thickness" of a film, for reference purposes herein, comprises the average distance between the top surface and the bottom surface of the film. The thickness of a film described herein can be measured in any manner not inconsistent with the objectives of the present invention. Moreover, the thickness of a film described herein, in some cases, can be selected based on the mold used to form the film and/or the amount of material used to form the film, as described further hereinbelow.

In addition, a film described herein, in some embodiments, can also be optically transparent. In some cases, a film described herein has an optical transparency or transmittance of at least about 90 percent between about 400 nm and about 700 nm. In some embodiments, a film described herein has an optical transparency of at least about 95 percent or at least about 99 percent between about 400 nm and about 700 nm. In some cases, a film described herein has an optical transparency between about 80 percent and about 100 percent, between about 90 percent and about 99.9 percent, or between about 95 percent and about 99.9 percent between about 400 nm and about 700 nm. In some cases, a film has an optical transparency recited herein through an entire range of wavelengths recited herein, such as an optical transparency of at least about 90 percent throughout the entire range of about 400 nm to about 700 nm. In other cases, a film has an optical transparency recited herein at one or more specific wavelengths, such as at 400 nm, 500 nm, 600 nm, and/or 700 nm. Additionally, in some embodiments, a film described herein has an optical transparency described herein even after immersion in saline solution for up to 30 days or for more than 30 days. "Optical transparency," for reference purposes herein, refers to the percent transmittance of light of the recited wavelength or wavelength range that is incident on a film having a thickness recited herein, such as a thickness of about 100 nm to about 20 µm. As understood by one of ordinary skill in the art, percent transmittance can be measured in any manner not inconsistent with the objectives of the present invention.

Moreover, a film described herein can have any combination of properties or features described herein not inconsistent with the objectives of the present invention. In some embodiments, for instance, a film described herein has a chemical composition recited herein, a semi-permeability described herein, a thickness described herein, and an optical transparency described herein.

II. Methods of Making a Film

In another aspect, methods of making a film are described herein. In some embodiments, a method of making a film comprises combining a first solution comprising Type I collagen with a second solution comprising one or more additional ECM proteins to provide a gel solution; disposing the gel solution in a mold; and drying the gel solution in the mold to provide a film. Moreover, in some cases, the first solution and/or second solution comprises a drug and/or antibody. Thus, in some instances, a film made by a method described herein also comprises a drug and/or antibody dispersed within the film or on a surface of the film. In some embodiments, a method described herein further comprises crosslinking the one or more additional ECM proteins. Additionally, a method of making a film described herein can also comprise removing the film from the mold. In some cases, the film is removed by peeling the film out of the mold, such as by using a pair of forceps. It is also possible to leave the film in the mold if desired. Moreover, in some cases, a method described herein further comprises sterilizing the film.

Turning now to steps of methods, methods of making a film described herein comprise combining a first solution comprising Type I collagen with a second solution comprising one or more additional ECM proteins to provide a gel solution. The Type I collagen can comprise any Type I collagen not inconsistent with the objectives of the present invention, including Type I collagen described hereinabove in Section I. In addition, Type I collagen can be present in the first solution in any amount not inconsistent with the objectives of the present invention. In some embodiments, for instance, the Type I collagen is present in the first solution in an amount between about 0.5 mg/mL and about 50 mg/mL, between about 1 mg/mL and about 15 mg/mL, between about 1 mg/mL and about 5 mg/mL, or between about 6 mg/mL and about 10 mg/mL.

Similarly, the one or more additional ECM proteins can comprise any additional ECM proteins not inconsistent with the objectives of the present invention, including one or more ECM proteins described hereinabove in Section I, such as Type IV collagen or laminin. Further, the additional ECM proteins can be present in the second solution in any amount not inconsistent with the objectives of the present invention. In some cases, for instance, the one or more ECM proteins are present in the second solution in an amount between about 0.5 mg/mL and about 30 mg/mL, between about 1 mg/mL and about 20 mg/mL, or between about 5 mg/mL and about 15 mg/mL.

In addition, the first solution and the second solution of a method described herein can be combined in any manner and in any amounts and ratios not inconsistent with the objectives of the present invention. For example, in some embodiments, the volume of the first solution is at least about 10 times, at least about 100 times, or at least about 1000 times the volume of the second solution. In some cases, the volume of the first solution is about 10 times to about 1000 times or about 10 times to about 100 times the volume of the second solution.

Moreover, the amounts of the Type I collagen and the additional ECM proteins in the gel solution can have any ratio not inconsistent with the objectives of the present invention. For example, in some instances, the weight ratio of Type I collagen to the additional ECM proteins in the gel solution is at least about 40:1 or at least about 50:1. In some embodiments, the weight ratio of Type I collagen to the additional ECM proteins in the gel solution is between about 40:1 and about 80:1, between about 40:1 and about 70:1, between about 40:1 and about 60:1, or between about 45:1 and about 55:1.

Moreover, in some cases, the first solution and/or second solution comprises a drug and/or antibody. Any drug or antibody not inconsistent with the objectives of the present invention may be used, including a drug or antibody described hereinabove in Section I. In addition, a drug and/or antibody can be present in the first and/or second solution in any amount not inconsistent with the objectives of the present invention. In some cases, for instance, a drug or antibody is present in the first or second solution in an amount between about 1 µg/mL and about 10 mg/mL or between about 10 µg/mL and about 1 mg/mL.

Methods of making a film described herein also comprise disposing a gel solution in a mold. A gel solution can be disposed in a mold in any manner not inconsistent with the objectives of the present invention. In some embodiments, for instance, the gel solution is poured into the mold. In some cases, the gel solution is spread within the mold using an instrument such as a pipet tip or a spatula. Further, any mold not inconsistent with the objectives of the present invention may be used. In some instances, the mold is formed from a polymer such as polydimethylsiloxane (PDMS). In other cases, the mold is formed from glass. In addition, the size and shape of a mold described herein, in some cases, can at least partially determine the size and shape of a film formed by a method described herein. Any size and shape not inconsistent with the objectives of the present invention may be used. In some cases, for example, a mold has a depth up to about 1 mm, up to about 200 µm, or up to about 100 µm. In some embodiments, a mold has a depth between about 10 µm and about 1 mm or between about 10 µm and about 100 µm.

Methods of making a film described herein also comprise drying a gel solution in a mold to provide the film. Drying can be carried out in any manner not inconsistent with the objectives of the present invention. In some embodiments, drying a gel solution in a mold comprises flowing a gas over the surface of the gel solution in the mold. Further, in some cases, the gas is flowed over the surface of the gel solution in a uniform or substantially uniform direction. In addition, in some instances, the gas is flowed over the surface of the gel solution in a non-turbulent manner. In some embodiments, for instance, the mold comprising the gel solution is disposed in a non-turbulent air-flow tunnel. Moreover, gas can be flowed at any rate not inconsistent with the objectives of the present invention. In some embodiments, for example, the gas is flowed at a rate of about 0.5 standard cubic feet per hour (SCFH) to about 3 SCFH or about 1 SCFH to about 2 SCFH. Any gas not inconsistent with the objectives of the present invention may be used. For instance, in some cases, the gas is air. In other cases, the gas is an inert gas such as nitrogen or argon.

Methods of making a film described herein, in some embodiments, also comprise crosslinking one or more additional ECM proteins. Crosslinking can be carried out in any manner not inconsistent with the objectives of the present invention. In some instances, crosslinking one more additional ECM proteins comprises irradiating the ECM proteins with ultraviolet (UV) light, including for a period between about 1 minute and about 60 minutes or between about 10 minutes and about 30 minutes.

Methods of making a film described herein, in some embodiments, also comprise removing the film from a mold. The film can be removed from the mold in any manner not inconsistent with the objectives of the present invention. In some cases, the film is removed by peeling the film out of the mold. Other methods of removing a film from a mold can also be used. It is also possible to leave the film in the mold if desired.

Moreover, in some cases, a method of making a film described herein further comprises sterilizing the film. A film made by a method described herein can be sterilized in any manner not inconsistent with the objectives of the present invention. In some cases, for instance, a film is sterilized by irradiating the film with UV light. In other cases, a film is sterilized by heating the film (up to 130° C.) or by exposing the film to a chemical treatment.

III. Articles Comprising a Film or Stack of Films

In another aspect, articles comprising a film or stack of films are described herein. In some embodiments, an article comprises a stack of films, wherein at least one film of the stack is a film described hereinabove in Section I. For example, in some cases, at least one film of the stack is formed from Type I collagen and one or more additional ECM proteins. In some instances, at least one film of the stack further comprises a top surface, a bottom surface in facing opposition to the top surface, and a plurality of cells disposed on the top surface of the film.

Additionally, in some embodiments, a plurality of films of the stack are films described hereinabove in Section I. For example, in some cases, a stack of films comprises (1) a first film comprising a first top surface, a first bottom surface in facing opposition to the first top surface, and a first plurality of cells disposed on the first top surface of the first film and (2) a second film comprising a second top surface, a second bottom surface in facing opposition to the second top surface, and a second plurality of cells disposed on the second top surface of the second film, wherein the first and second films are arranged in a stacked configuration and are each formed from Type I collagen and one or more additional ECM proteins. Further, the chemical composition of the first film and the second film can be the same or different. Similarly, the first plurality of cells can comprise the same or a different type of cells than the second plurality of cells.

Moreover, stacks of films described herein are not limited to stacks comprising two films described herein. Instead, if desired, stacks of films described herein can further comprise any desired number of additional films described herein. Thus, articles described herein, in some embodiments, can comprise a stack of three films, four films, five films, or more than five films described herein. Further, in some cases, a stack of films described herein is free or substantially free of a glue or adhesive material disposed between the films.

In addition, an article comprising a stack of films described herein can have any size and/or shape not inconsistent with the objectives of the present invention. In some cases, for instance, a stack of films can be rolled into a tubular shape. Thus, in some embodiments, an article described herein can be a vascular graft or a model for a biological organ or compartment such as a blood vessel. A vascular graft formed from a stack of films described herein, in some embodiments, can have an inner diameter between about 0.5 mm and about 10 mm or between about 1 mm and about 5 mm. In other cases, an article described herein can be a lung model or a blood-brain model.

Additionally, in some embodiments, an article described herein comprises a film described hereinabove in Section I in combination with another film or material. For example, in some cases, an article described herein comprises a first film formed from Type I collagen and one or more additional ECM proteins and a second film formed from a hydrogel, wherein the first film and the second film have differing mechanical stiffness and are immediately adjacent to one another in a stacked configuration. The hydrogel can comprise any hydrogel not inconsistent with the objectives of the present invention. In some embodiments, for instance, the hydrogel comprises a hyaluronic acid hydrogel. In addition, in some cases, an article described herein further comprises a population of cells disposed on a surface of the article, such as a surface of the first film or the second film or a surface that includes an interface between the first film and the second film. In implementations, for example, the surface can be substantially parallel or substantially perpendicular to the plane of the interface between the first film and the second film. As described further hereinbelow, articles having such a construction, in some cases, can provide a model system for studying the dependence of a cell's phenotype on the mechanical stiffness of a medium on which the cell is disposed, such as the migration, polarity, and proliferation of the cell.

In other exemplary embodiments, an article described herein comprises a film described hereinabove in Section I, a first block comprising a first microchannel, and a second block comprising a second microchannel, wherein the film is disposed between and immediately adjacent to the first block and the second block and the first microchannel and the second microchannel are in fluid communication with the film. The film can have any composition and/or properties of a film described hereinabove in Section I. In some cases, for instance, the film is semi-permeable. In addition, the first and second blocks of an article described herein can be formed from any material and have any structure not inconsistent with the objectives of the present invention. In some embodiments, for instance, the first block and/or the second block is formed from a micro-patterned polymer, glass, or semiconductor material. For example, in some cases, the first block and the second block each comprise a micro-patterned PDMS block. Therefore, in some embodiments, an article described herein can be a microfluidic device wherein a film described herein acts as a semi-permeable membrane between microchannels or micro-patterned blocks disposed on opposite sides of the membrane film.

IV. Methods of Making a Stack of Films

In another aspect, methods of making a stack of films are described herein. In some embodiments, a method of making a stack of films comprises providing a first film described hereinabove in Section I; providing a second film described hereinabove in Section I; wetting the top surface of the first film with water; and stacking the second film on the first film, wherein the bottom surface of the second film contacts the water disposed on the top surface of the first film to provide a wet interface between the stacked first and second films. In some embodiments, a method of making a stack of films further comprises drying the interface between the stacked first and second films.

For example, in some implementations, a method of making a stack of films comprises (1) providing a first film comprising a first top surface and a first bottom surface in facing opposition to the first top surface, wherein the first film is formed from Type I collagen and one or more additional ECM proteins; (2) providing a second film comprising a second top surface and a second bottom surface in facing opposition to the second top surface, wherein the second film is formed from Type I collagen and one or more additional ECM proteins; (3) wetting the first top surface of the first film with water; (4) stacking the second film on the first film, wherein the second bottom surface of the second film contacts the water disposed on the first top surface of the first film to provide a wet interface between the stacked first and second films; and (5) drying the interface between the stacked first and second films.

Further, in some cases, a method described herein can also comprise providing one or more additional films described hereinabove in Section I and repeating the wetting, stacking, and drying steps to provide a stack of films comprising any desired number of films. In some embodiments, for instance, a method further comprises (6) providing a third film comprising a third top surface and a third bottom surface in facing opposition to the third top surface, wherein the third film is formed from Type I collagen and one or more additional ECM proteins; (7) wetting the second top surface of the second film with water; (8) stacking the third film on the second film, wherein the third bottom surface of the third film contacts the water disposed on the second top surface of the second film to provide a wet interface between the stacked second and third films; and (9) drying the interface between the stacked second and third films.

Turning now to steps of methods, methods of making a stack of films described herein comprise providing a first film, a second film, and, in some cases, one or more additional films. The first film, second film, and any additional film of a method described herein can have the structure or properties of any film described hereinabove in Section I, including a film comprising a plurality of cells disposed on a surface of the film. Further, any two films used in a method described herein can have the same or different properties. For example, in some cases, a first film comprises a first plurality of cells of a first type and a second film comprises a second plurality of cells of a second type. Moreover, in some embodiments, the first film comprises a first plurality of cells disposed on the first top surface of the first film and the second film comprises a second plurality of cells disposed on the second top surface of the second film prior to stacking the first film and the second film. Therefore, a method of making a stack of films described herein, in some embodiments, can provide a stack of films suitable for use as a tissue scaffold, cell culture substrate, and/or tissue model, including a scaffold, cell culture substrate, and/or tissue model having a complex or layered configuration of cell types. In addition, in some embodiments, a method described herein can be used to form an article described hereinabove in Section III.

Methods of making a stack of films described herein also comprise wetting the top surface of the first film with water. Any amount of water not inconsistent with the objectives of the present invention may be used. In some cases, only a portion or limited area of the top surface of the first film is wetted. In other instances, the entire top surface of the first film is wetted.

Methods of making a stack of films described herein also comprise stacking the second film on the first film. Stacking can be carried out in any manner not inconsistent with the objectives of the present invention. In some embodiments, the bottom surface of the second film is disposed entirely on the top surface of the first film. In other instances, the bottom surface of the second film is partially disposed on the top surface of the first film, such that a portion of the bottom surface of the second film may overhang or extend beyond the top surface of the first film. Further, in some embodiments, the second film is stacked on the first film at an angle, such as a 90 degree angle within the plane of the interface. Moreover, methods of making a stack of films described herein, in some embodiments, do not comprise disposing a glue or adhesive material between films of the stack before, during, or after stacking the films. Avoiding the use of a glue or adhesive, in some cases, can permit the formation of a layered structure or article comprising healthy living cells.

Methods of making a stack of films described herein, in some embodiments, also comprise drying the interface between the stacked films. Drying can be carried out in any manner not inconsistent with the objectives of the present invention. In some embodiments, for example, drying is carried out by flowing a gas over the stacked films. Any gas not inconsistent with the objectives of the present invention may be used. In some cases, the gas is an inert gas such as nitrogen or argon. Moreover, in some embodiments, the gas is free or substantially free of water. A gas that is "substantially free" of water, in some embodiments, comprises less than about 1000 parts per million (ppm), less than about 100 ppm, or less than about 10 ppm water.

Some embodiments described herein are further illustrated in the following non-limiting examples.

Example 1

Films

Films according to some embodiments described herein were prepared as follows. To prepare a film described herein, a first gel solution (1 mL) was first prepared by combining a first solution of sterile Type I collagen derived from rat tail (at a concentration of 3 mg/mL in 0.02N acetic acid) with a second solution (20 µL) comprising one or more additional ECM proteins (at a concentration of 8-12 mg/mL). Specifically, an ECM gel from Engelbreth-Holm-Swarm mouse sarcoma (Sigma) was used. In some cases, a drug and/or antibody was also added to the second solution at a concentration described herein. The vial in which the gel solution was prepared was pre-cooled to 4° C. to prevent denaturation of the proteins. In addition, the gel solution was stored at 4° C. until ready for use.

Next, a mold was prepared. Specifically, a rectangular well pattern having dimensions of 0.8 cm (width)×1.2 cm (length)×100 µm (height) was prepared on a 4-inch silicon wafer using photolithography. This pattern was then transferred onto PDMS using the manufacturer's protocol to obtain a PDMS mold with a rectangular well having the dimensions above. The PDMS mold was then cleaned using Scotch tape.

Following preparation of the mold, 40-200 µL of the gel solution was pipetted into the PDMS mold. The solution was then spread evenly in the mold using the pipette tip. The mold was then placed in a custom built air-flow tunnel. The gel solution was air-dried in the mold at a very low air flow (0.5-0.9 SCFH), allowing the gel solution to dry evenly over a period of 60-90 minutes. After the mixture was completely dried, the mold was placed under a long-wave UV lamp (100 W, 365 nm) for 25 minutes to crosslink the ECM proteins. The mold was allowed to cool for 3-4 hours. Then, using a clean pair of forceps, the air-dried film was gently peeled out of the mold. To use this film for cell culture applications, the film was sterilized in a bio-safety cabinet under UV light (254 nm) for 30 minutes.

Some steps of the foregoing process are represented schematically in FIG. 1.

After fabricating films as described above, the films were characterized as follows. Film samples were prepared in the same manner for all the characterization studies. Specifically, a free-standing film was placed in a 60 mm petri dish with a glass cover slip (22×22 mm) placed inside. The dish containing the film was filled with phosphate buffered saline (PBS) and allowed to sit for 60 seconds to neutralize the acetic acid from the collagen solution. The PBS was then drained from the dish and deionized water was added to the same petri dish to remove the salts present in PBS. The DI water was slowly drained from the petri dish after one minute, ensuring that the film was deposited on the cover slip. The film was made to stick on the cover slip by drying the film with nitrogen gas. The nitrogen gas was gently blown over the entire length of the film.

To confirm the presence of Type I collagen and laminen, the film was fixed with 4% para-formaldehyde in PBS and double immunostained for laminin (RbIgG, 1:500, Sigma) and Type I collagen (mIgG1, 1:200, Sigma). Secondary antibodies were goat anti-RbIgG Dylight 488 (1:220, Jackson ImmunoResearch) for laminin and goat anti-mIgG1 Dylight 594 for Type I collagen. The film showed positive for the laminin and Type I collagen antibodies, indicating that the proteins were not denatured by the air drying and the UV crosslinking.

The thickness of the film was measured by profilometry (Alpha Step IQ profilometer). Each sample was measured multiple times in different areas of the film. An average thickness of 0.607 microns with a standard deviation of 0.278 microns was obtained for 6 samples.

The surface roughness $R_a$ was measured by atomic force microscopy (Dimension 500 AFM). The average surface roughness $R_a$ for 6 samples, each measured in multiple areas between two random points on the film surface, was 156.873 nm, with a standard deviation of 42.585 nm. The surface topography of the film was also observed by scanning electron microscope (Zeiss Supra 55VP SEM). For surface topography observation, three samples were sputter coated with gold metal having a thickness of 15 nm and scanned at a magnification of 1000×.

Example 2

Films Comprising Cells

Films comprising a plurality of cells disposed on a surface of the films according to some embodiments described herein were prepared in two ways as follows. In the first technique, a film was prepared and attached to a cover slip as described above in Example 1. The cover slip was placed in a bio-safety cabinet and exposed to UV light (254 nm) for 30 minutes for sterilizing the film. The cover slip was then transferred to a sterile 35 mm petri dish and incubated overnight in a cell culture medium at 37° C. and 5% $CO_2$. This method provided a so-called "fixed" film comprising a plurality of cells on the top surface of the film.

In the second technique, a film was prepared and peeled out of a PDMS mold, crosslinked with UV light, and sterilized in a bio-safety cabinet for 30 minutes under UV light as described above in Example 1. A cell culture medium was added to a 60 mm petri dish, and the film was held with a pair of forceps and gently placed in the medium. The film floated in the medium without curling, folding, or deforming. The petri dish was incubated overnight at 37° C. and 5% $CO_2$. This method provided a so-called "floating" film comprising a plurality of cells on the top surface of the film.

Six different primary cells were cultured on either the floating or fixed films described above: human aortic endothelial cells (HAEC), human glioblastoma multiforme (hGBM) cells, human aortic smooth muscle cells (HASMC), human fibroblasts, human astrocytes and E-18 derived rat cortical neurons. hGBM cells were cultured in serum-free tumor medium (DMEM/F-12 supplemented with B-27 (Invitrogen)), Insulin Transferrin Selenium-X (Invitrogen), gentamycin (50 µg/mL, Invitrogen), 20 ng/mL mouse epidermal growth factor, and 20 ng/mL basic fibroblast growth factor. HAEC, HASMC, human fibroblasts, and human astrocytes were cultured in DMEM/F-12 medium containing 10% fetal bovine serum. E-18 derived rat cortical neurons were cultured in Neurobasal medium supplemented with B-27, gentamycin, brain derived neurotrophic factor (10 ng/mL, Peprotech) and neutrotrophin-3 (10 ng/mL, Peprotech).

For further characterization, cells grown on a film as described herein were fixed with 4% paraformaldehyde in PBS and immunostained for the following markers: EGFR (mIgG2b, Sigma, 1:500) and laminin (RbIgG, Sigma, 1:500) for hGBM cells; VWF (Von Willebrand factor, RbIgG, Santa cruz biotech, 1:200) for HAEC; Smooth muscle actin (mIgG2a, AbDSerotec, 1:200) for HASMC; Vimentin (mIgG1, Sigma, 1:500) for human fibroblasts; GFAP (RbIgG, Dako, 1:1000) for human astrocytes; and beta III tubulin (mIgG2b, Sigma, 1:500) for cortical neurons.

Cells of all types described above were observed to attach and proliferate well on both the "fixed" and the "floating" films. Cell growth on the floating film indicated that the film was semi-permeable and permitted the cells on the top surface of the film to receive nutrition from the cell culture medium in contact with the bottom surface of the film.

Example 3

Stacks of Films

Stacks of films according to some embodiments described herein were prepared in two ways as follows. In the first technique, films prepared as described in Example 1 were mounted on an aluminum support. Specifically, a sheet of aluminum foil was cut into rectangles of approximate dimensions 2.5 cm (width)×2 cm (length)×0.001 inches (height). A circular punch having a diameter of 8 mm was made in the center of each rectangular portion of aluminum foil to provide an aluminum support. The aluminum support was then sterilized by soaking in 70% ethanol for 20 minutes. Next, the aluminum support was washed with sterilized de-ionized water twice in a bio-safety cabinet and left to dry.

An air-dried film prepared as described in Example 1 was sterilized by exposing it to UV light in a bio-safety cabinet for 30 minutes. After the sterilization, the film was attached to a rectangular aluminum support described above using PBS. Specifically, the aluminum support was placed in a petri dish. Using a pair of forceps, the film was gently lifted and held firmly on the aluminum support in such a way so as to position the circular punch hole of the aluminum support in the center of the film. PBS was then added onto the four corners of the film using a micropipette. This application of PBS secured the film onto the aluminum support. This process was repeated to provide a stack of films, where each film adhered to an aluminum support described herein served as one individual layer of the stack.

To obtain a stack of films comprising cells on the surfaces of the films of the stack using this technique, individual layers of the stack were first used as a cell culture substrate prior to combining the individual layers into a stack as described above. Specifically, each layer of the stack of films was separately placed in a petri dish containing cell culture medium prior to combining the layers to form the stack. Each film and its corresponding aluminum support was incubated in the cell culture medium overnight at 37° C. and 5% $CO_2$. After the overnight incubation, the medium was replaced with fresh cell culture medium. In this manner, a desired cell type was seeded and grown on each film. The stack of films was then prepared as described above using the cell-containing films.

Figure 2:
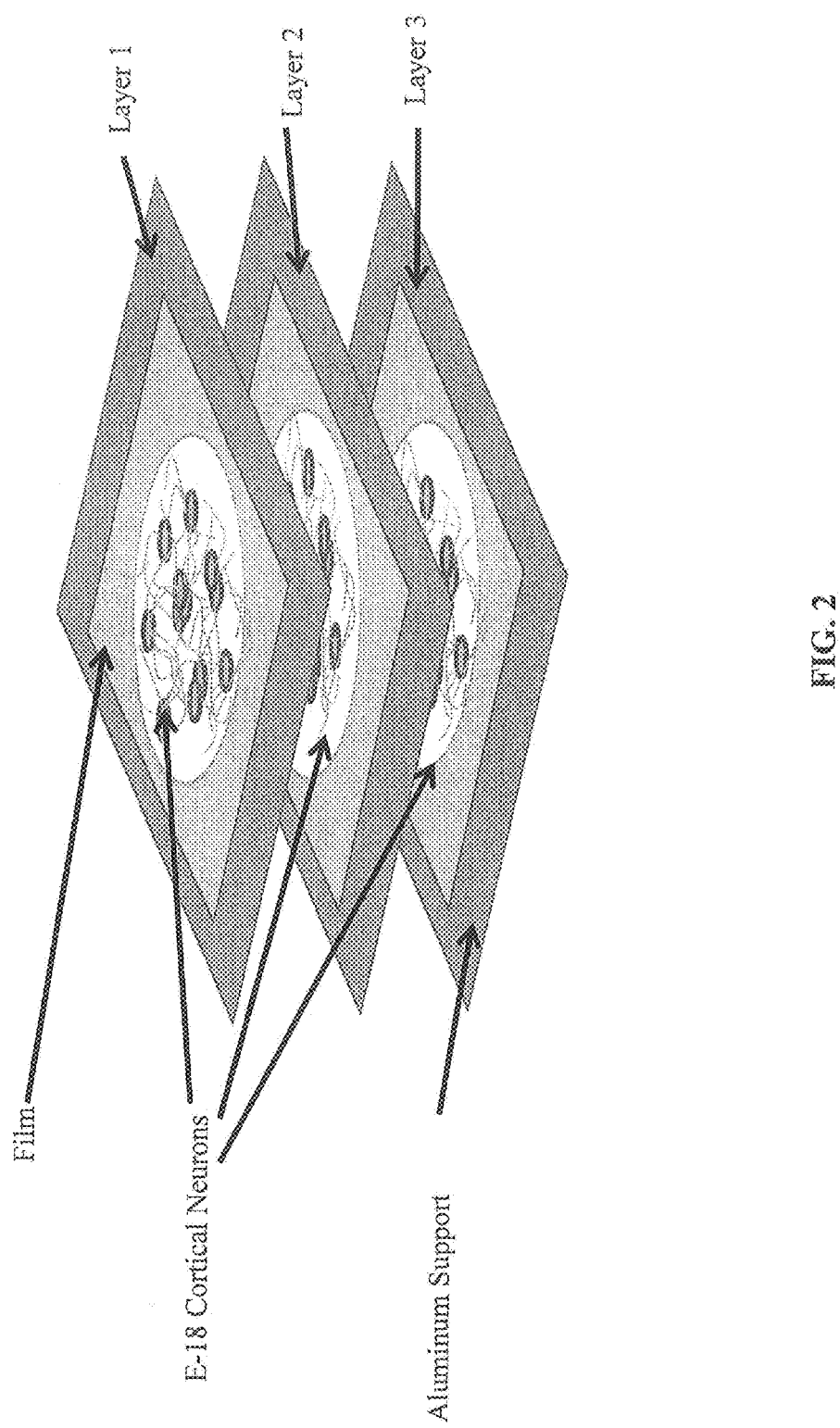
FIG. 2 illustrates an exploded view of a stack of films according to one embodiment described herein.

For example, in one case, the foregoing technique was used to prepare a stack of three films, each film comprising cortical neurons disposed on the top surface of the film. The cortical neuron cells were seeded onto the three films individually as described herein and allowed to grow for 3-4 days at 37° C. and 5% $CO_2$. The medium was replaced with fresh medium with growth factors every 2 days. After 3-4 days, the neurons showed sufficient growth for the three layers or films to be stacked to make the three-dimensional stack of films. In this case, the individual layers were stacked and further held together with the help of a PDMS block. The PDMS block had an opening made by multiple punches using an 8 mm biopsy punch. The PDMS block had an approximate thickness of 5 mm and was sterilized using 70% ethanol. After the stack was formed, the PDMS block was gently placed onto the top of the stack to hold the layers of the stack together. Once assembled, the stack of films served as a neuron cell culture model. Specifically, the entire cell culture model was incubated at 37° C. and 5% $CO_2$ for 4-5 days to allow the axons from one layer of neuron cells to grow into the adjacent layers. FIG. 2 illustrates an exploded view of such a stack of films comprising cortical neurons as described herein.

Figure 3:
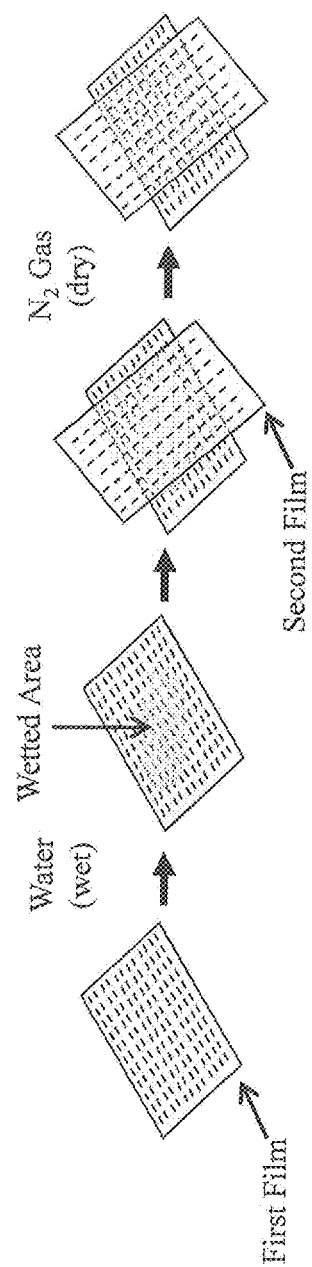
FIG. 3 illustrates a perspective view of a method of making a stack of films according to one embodiment described herein.

In the second technique, a stack of films was prepared without the use of an aluminum support. Specifically, films were stacked by simply wetting and drying the interface between adjacent films. FIG. 3 illustrates this process schematically. With reference to FIG. 3, a first film described herein and a second film described herein were provided. The top surface of the first film was wetted with water to provide a wetted area. The second film was then stacked on the first film so that the bottom surface of the second film contacted the water disposed on the top surface of the first film to provide a wet interface between the stacked first and second films. The interface was then dried by flowing nitrogen over the stacked films.

As with the first technique described above, the second technique could also be carried out using films comprising cells disposed on their top surfaces. Such films could be provided as described in Example 3 above and then stacked using the process illustrated in FIG. 3.

Example 4

Article Comprising a Film

Figure 4:
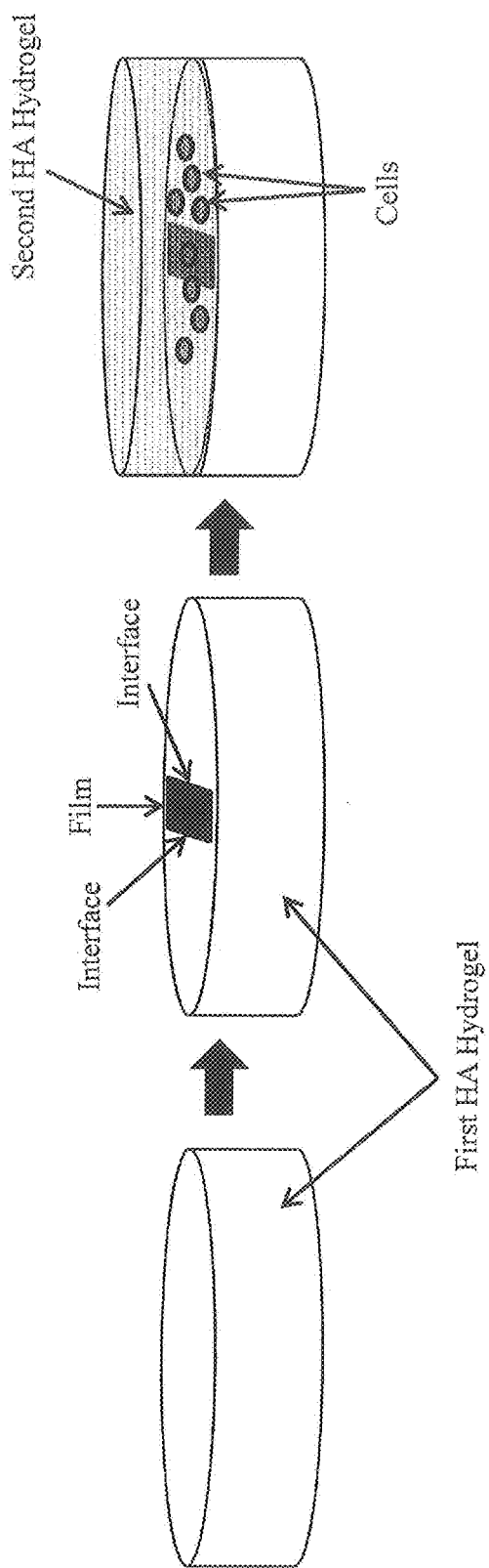
FIG. 4 illustrates a perspective view of a method of making an article comprising a film according to one embodiment described herein.

An article comprising a film according to one embodiment described herein was prepared as follows. With reference to FIG. 4, a film was first prepared as described in Example 1. Next, a commercially available hyaluronic acid (HA) hydrogel film having a different mechanical stiffness than the film according to Example 1 was placed on a cell culture plate. While the HA hydrogel film was still in liquid form, the film according to Example 1 was placed on the top of the hydrogel film. The hydrogel film was then solidified, thereby providing an article comprising stacked films having different mechanical stiffnesses but a physically continuous interface.

Figure 5:
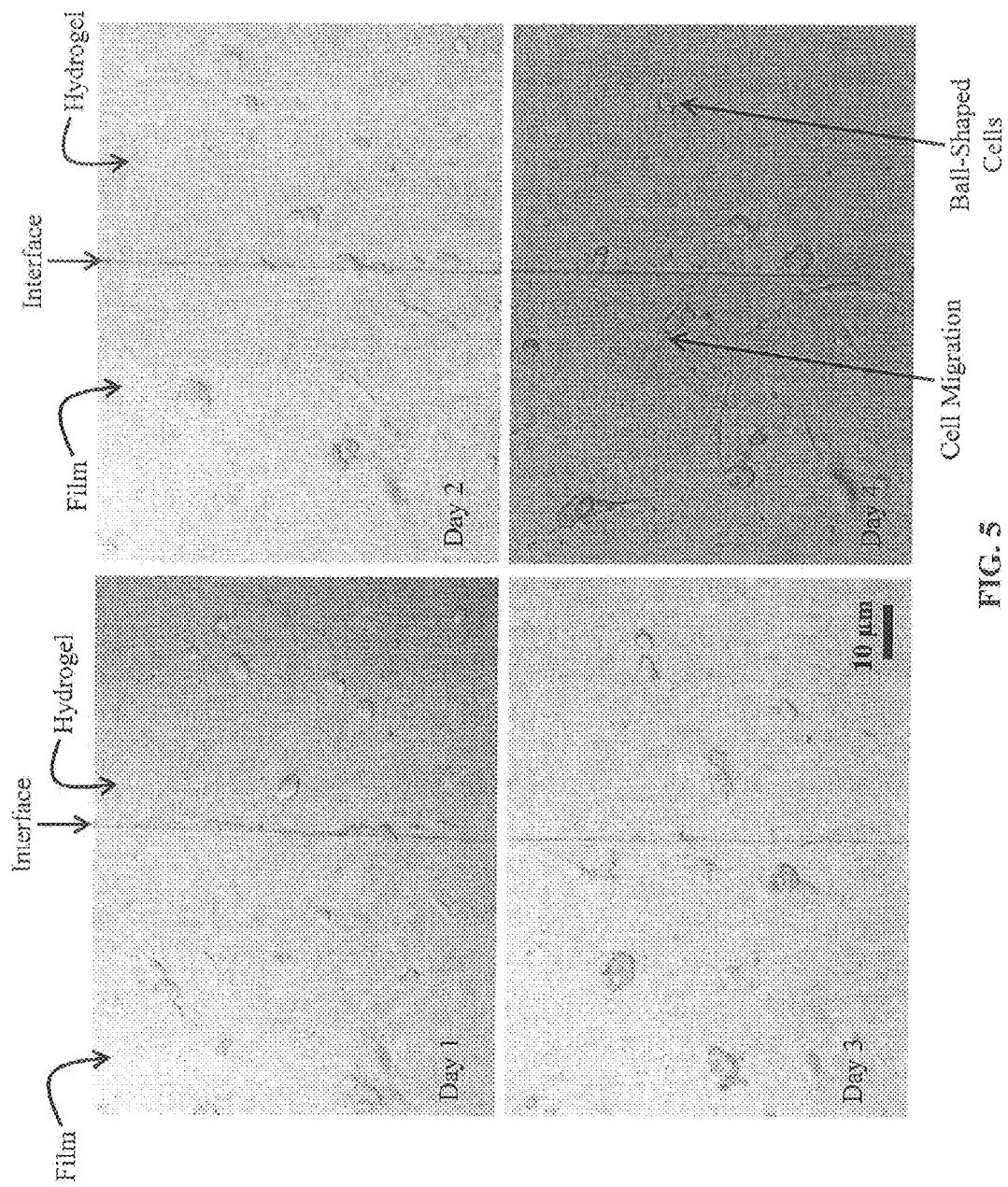
FIG. 5 illustrates a plan view of an article comprising a film according to one embodiment described herein.

Following formation of the foregoing article, the article was used to study and influence the phenotype of cancer cells. Specifically, brain cancer cells were mixed with a second HA hydrogel and then applied on top of the article. In particular, the cancer cells were applied on the surface of the article comprising the interface between the film according to Example 1 and the first HA hydrogel film. As illustrated in FIG. 5, the cells began to change their phenotype in response to the differing stiffnesses of the adjacent films. FIG. 5 shows microscope images of the interface between the film according to Example 1 ("Film") and the first HA hydrogel film ("Hydrogel") at 1 day, 2 days, 3 days, and 4 days following addition of the cancer cells to the article. On top of the film according to Example 1, the cells were elongated and actively migrated. In contrast, the cells remained in a ball shape when on the HA hydrogel. Thus, the article comprising a film described herein was used to influence cell phenotypes such as migration, polarity, and proliferation.

Example 5

Microfluidic Device

A microfluidic device comprising a film according to one embodiment described herein was prepared as follows. Specifically, a microfluidic device was prepared for gas exchange applications. The device comprised a semi-permeable film described herein and two micro-patterned PDMS blocks. In particular, the semi-permeable film was disposed between and immediately adjacent to a first PDMS block comprising a first microchannel and a second PDMS block comprising a second microchannel. In addition, the first microchannel and the second microchannel were designed to be in fluid communication with the semi-permeable film.

To prepare the device, standard microfabrication techniques were used. First, a mask was designed for the fabrication of a silicon wafer template for the device. The microfluidic pattern of the silicon wafer was designed using AutoCAD. The mask was then fabricated using standard fabrication techniques. Specifically, the materials used for fabricating the wafer included a 4-inch silicon wafer, SU8-50 photoresist (Microchem), SU8 developer (Microchem), and acetone. The machines used for fabricating the wafer included hot plates, a spin coater, and a back-side aligner.

The wafer was fabricated as follows. First, the silicon wafer was washed with acetone and dehydrated by baking at 200° C. for ten minutes. Next, the wafer was coated with SU8-50 photoresist by pouring the resist onto the wafer and spinning at 500 rpm at 100 rpm/s for 10 seconds, followed by spinning at 1000 rpm at 300 rpm/s for 30 seconds. After the wafer was coated, it was baked at 65° C. for 10 minutes followed by baking at 95° C. for 30 minutes. The photoresist was then polymerized using UV light irradiation (350-400 nm, 300-550 mJ/cm$^2$). The duration of UV exposure was based on the manufacturer's protocol for obtaining the desired height of the pattern. For obtaining a height of 100 microns, the UV exposure time was 28 seconds. Next, to crosslink the exposed regions of the resist, the wafer was baked at 65° C. for 1 minute and at 95° C. for 10 minutes. The unexposed parts of the wafer which were not cross-linked were then rinsed using the SU8 developer. The wafer was next immersed in the developer and washed rigorously for 10 minutes, followed by blow drying using nitrogen. Finally, the wafer was hard baked at 150° C. for 30 minutes.

Following fabrication of the silicon wafer, the micro-patterned PDMS blocks were prepared using a SYLGARD® 184 elastomer kit (DowCorning). The curing agent and PDMS were mixed in a 1:10 ratio (6 mL of curing agent:60 mL of PDMS). The mixture was then placed in a vacuum dessicator under a pressure of 20 mm Hg for 1 hour to remove all the air bubbles created by the mixing process. The PDMS mixture was removed from the dessicator only after all the air bubbles were removed from the mixture. Next, the silicon wafer fabricated as described above was wrapped in aluminum foil and placed on a hot plate at 70° C. The PDMS mixture was then poured onto the wafer and any air bubbles introduced into the mixture while pouring were removed with a sharp pair of forceps. Next, the wafer was placed on a hot plate at 150° C. for 5 minutes to allow the PDMS to cure and crosslink. After the PDMS cured completely, the wafer was placed on the hot plate at 70° C. and the patterned PDMS was cut out using a scalpel blade. After formation of the micro-patterned PDMS blocks, a biopsy punch was used to create 2 mm punches in each block to be used for inlets and outlets, as described further below.

Figure 6:
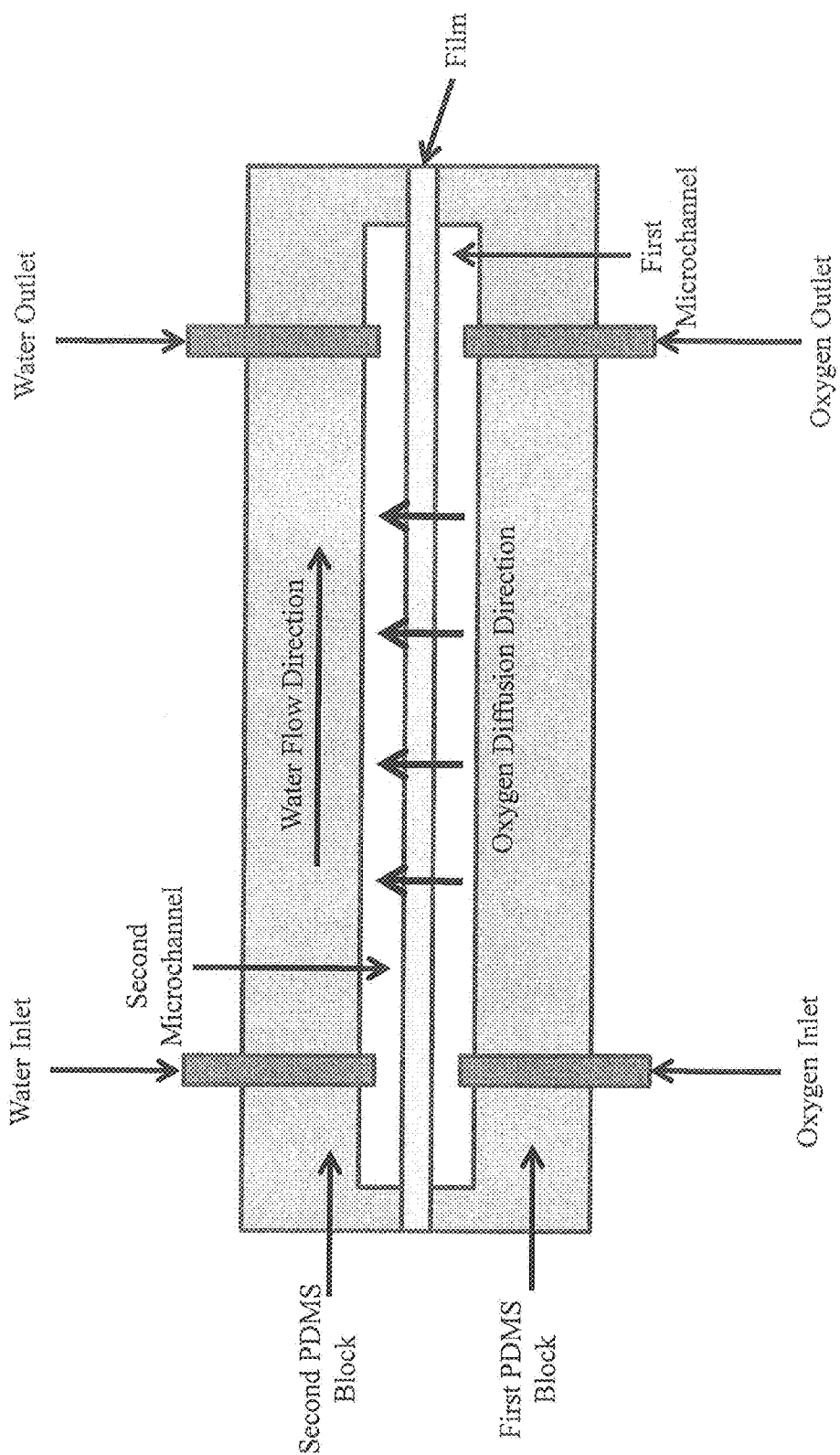
FIG. 6 illustrates a sectional view of an article comprising a film according to one embodiment described herein.

The semi-permeable film used for the microfluidic device was prepared as described in Example 1, except the mold dimensions were 2 mm×2 mm×100 µm and the concentration of Type I collagen in the first solution was altered to 6 mg/mL to provide a film permeable to air/oxygen but impermeable to water (when the Type I collagen concentration was 3 mg/mL, the film was permeable to both air/oxygen and water). The semi-permeable film was placed on the first micro-patterned PDMS block, which included a microchannel for transporting oxygen, as shown in FIG. 6. The second micro-patterned PDMS block, which included a microchannel for transporting water, was then placed face-up (with the microchannel on top) in a UV-ozone plasma chamber, along with the first PDMS block comprising the semi-permeable film. Both PDMS blocks (and the semi-permeable film) were exposed to UV light for 10 minutes. After UV exposure, the micro-patterned blocks were placed on top of one another in a stacked configuration, with the semi-permeable film being sandwiched between them. The microchannels for water and air/oxygen were therefore separated by the semi-permeable film. Plasma treatment was then carried out. The plasma treatment helped bind the two PDMS blocks together. The device was then left overnight to further bond the PDMS blocks.

After permanently bonding the PDMS blocks and semi-permeable membrane together to form the microfluidic device, the device was connected to an oxygen/air source and a water source. The oxygen/air inlet was connected to a first microchannel of the first PDMS block through a 2 mm punch of the first PDMS block. The input pressure of oxygen was set to 0.1 SCFH. The outlet pipe for the oxygen/air was provided at the other end of the first microchannel via another 2 mm punch. Similarly, a water inlet was connected to a second microchannel of the second PDMS block through a 2 mm punch of the second PDMS block. A water outlet was provided at the other end of the second microchannel via another 2 mm punch. Air was flowed through the first microchannel of the first PDMS block, and water was flowed through the second microchannel of the second PDMS block. The water was flowed at a flow rate of 0.6 mL/hour. Water exiting the device through the water outlet was collected in a beaker. Water and air were flowed through the device in this manner for 20 minutes, and 2 mL of oxygenated water was collected. The concentration of dissolved oxygen in the water was measured before and after running the experiment using a dissolved oxygen meter (Mettler Toledo SG6). The change in the concentration of dissolved oxygen was statistically significant with a p-value <0.01. Prior to flowing through the device as described herein, the water had an average dissolved oxygen concentration of 6.93 ppm (standard deviation of 0.10 ppm). After flowing through the device, the water had an average dissolved oxygen concentration of 7.098 ppm (standard deviation of 0.14 ppm).

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A film comprising:
   a top surface; and
   a bottom surface in facing opposition to the top surface,
   wherein the film is formed from Type I collagen and one or more additional extracellular matrix proteins,
   wherein the Type I collagen is not crosslinked,
   wherein the film has an average thickness of 100 nm to 20 µm and an optical transparency of at least 90 percent between 400 nm and 700 nm, and
   wherein the Type I collagen comprises aligned or substantially aligned collagen fibrils.

2. The film of claim 1, wherein the additional extracellular matrix proteins comprise one or more of Type IV collagen, laminin, vitronectin, and fibronectin.

3. The film of claim 1, wherein the weight ratio of Type I collagen to the additional extracellular matrix proteins is at least 40:1.

4. The film of claim 1, wherein the film is semi-permeable.

5. The film of claim 1, wherein the film has a surface roughness $R_a$ of 50 nm to 250 nm.

6. The film of claim 1 further comprising:
   a plurality of cells disposed on the top surface of the film.

7. A method of making the film of claim 1, comprising:
   combining a first solution comprising Type I collagen with a second solution comprising one or more additional extracellular matrix proteins to provide a gel solution;
   disposing the gel solution in a mold; and
   drying the gel solution in the mold to provide a film, wherein drying the gel solution in the mold comprises flowing a gas over the surface of the gel solution in the mold.

8. The method of claim 7, wherein the weight ratio of Type I collagen to additional extracellular matrix protein in the gel solution is at least about 40:1.

9. The method of claim 7 further comprising crosslinking the one or more additional extracellular matrix proteins.

10. An article comprising:
a stack of films, wherein at least one film of the stack is the film of claim 1.

11. The article of claim 10, wherein the at least one film further comprises a plurality of cells disposed on the top surface of the film.

12. The article of claim 11, wherein the stack of films comprises a plurality of the films of claim 1.

13. An article comprising:
a first film comprising the film of claim 1; and
a second film formed from a hydrogel,
wherein the first film and the second film have differing mechanical stiffnesses and are immediately adjacent to one another in a stacked configuration.

14. An article comprising:
the film of claim 1, wherein the film of claim 1 is semi-permeable;
a first block comprising a first microchannel; and
a second block comprising a second microchannel,
wherein the semi-permeable film is disposed between and immediately adjacent to the first block and the second block and the first microchannel and the second microchannel are in fluid communication with the semi-permeable film.

15. A method of making a stack of films comprising:
providing a first film, wherein the first film is the film of claim 1;
providing a second film comprising a top surface and a bottom surface in facing opposition to the top surface, wherein the second film is formed from Type I collagen and one or more additional extracellular matrix proteins;
wetting a top surface of the first film with water;
stacking the second film on top of the first film, wherein the bottom surface of the second film contacts the water disposed on the first top surface of the first film to provide a wet interface between the stacked first and second films; and
drying the interface between the stacked first and second films.

16. The method of claim 15 further comprising:
providing a third film comprising a top surface and a bottom surface in facing opposition to the top surface, wherein the third film is formed from Type I collagen and one or more additional extracellular matrix proteins;
wetting the top surface of the second film with water;
stacking the third film on top of the second film, wherein the bottom surface of the third film contacts the water disposed on the top surface of the second film to provide a wet interface between the stacked second and third films; and
drying the interface between the stacked second and third films.

17. The method of claim 15, wherein the first film further comprise a first plurality of cells disposed on the top surface of the first film and the second film further comprise a second plurality of cells disposed on the top surface of the second film prior to stacking the first film and the second film.

18. The film of claim 1, wherein the weight ratio of Type I collagen to the additional extracellular matrix proteins is between 40:1 and 80:1.

19. The film of claim 1, wherein the film has an average thickness of 300 nm to 1 μm.

20. The film of claim 1, wherein the film is self-supporting.

21. The film of claim 1, wherein:
the film is semi-permeable;
the film has a surface roughness $R_a$ of 50 nm to 250 nm; and
the film is self-supporting.

* * * * *

UNITED STATES PATENT AND TRADEMARK OFFICE
CERTIFICATE OF CORRECTION

| | | |
|---|---|---|
| PATENT NO. | : 9,644,177 B2 | |
| APPLICATION NO. | : 13/940739 | |
| DATED | : May 9, 2017 | |
| INVENTOR(S) | : Young-Tae Kim et al. | |

It is certified that error appears in the above-identified patent and that said Letters Patent is hereby corrected as shown below:

In the Claims

Claim 15, Column 20, Line 3, please delete "first top surface" and replace with --top surface--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*